United States Patent
Williams (12)

(10) Patent No.: US 6,171,593 B1
(45) Date of Patent: Jan. 9, 2001

(54) METHOD OF TREATING SKIN DISORDERS USING AN EXTRACT OF MULLEIN

(76) Inventor: Johnny L. Williams, 7315 State Road-B, Dittmer, MO (US) 63023

( * ) Notice: Under 35 U.S.C. 154(b), the term of this patent shall be extended for 0 days.

(21) Appl. No.: 08/855,322

(22) Filed: May 13, 1997

Related U.S. Application Data

(62) Division of application No. 08/634,666, filed on Apr. 18, 1996, now abandoned, which is a continuation of application No. 08/337,122, filed on Nov. 10, 1994, now abandoned.

(51) Int. Cl.[7] .................................................. A61K 35/78
(52) U.S. Cl. ...................... 424/195.1; 424/400; 514/859; 514/861; 514/862; 514/863; 514/864; 514/865
(58) Field of Search ................................ 424/195.1, 400; 514/859–865

(56) References Cited

U.S. PATENT DOCUMENTS 4,767,618 * 8/1988 Grollier .................................. 424/74

OTHER PUBLICATIONS

Czygan in Herbal drugs and phytopharmaceuticals, pp. 518–519, 1994.*
Morton, in Folk remedies of Low country, pp. 155–157.*

* cited by examiner

*Primary Examiner*—Gollamudi S. Kishore
(74) *Attorney, Agent, or Firm*—Waddey & Patterson; I. C. Waddey, Jr.

(57) ABSTRACT

A method of treating skin disorders using a extract from the plant Mullein (genus Verbascum) and a composition including an extract from the plant Mullein (genus Verbascum) are described. The extract is obtained by cooking the leaves and roots of the plant Mullein in a pressure cooker with water. The resulting liquid extract is canned according to standard home canning procedures. The method is accomplished by applying the liquid extract to affected areas of the skin twice daily. Most subjects experience positive results within a period of approximately two weeks. Skin disorders that have been treated using this extract include the sun exposure related skin disorders, actinic keratoses, lentigines, seborrheic keratoses, and the inflammatory skin disorders including prurigo, psoriasis, and contact dermatitis. The skin cancer, malignant melanoma, has also been treated using this method.

21 Claims, No Drawings

METHOD OF TREATING SKIN DISORDERS USING AN EXTRACT OF MULLEIN

This is a divisional application of U.S. patent application Ser. No. 08/634,666 filed Apr. 18, 1996, for "Method for Treating Skin Disorders Using an Extract of Mullein", now abandoned, which is a continuation of application Ser. No. 08/337,122, filed Nov. 10, 1994, now abandoned.

BACKGROUND OF THE INVENTION

The present invention relates generally to the treatment of skin disorders and more particularly to the treatment of skin disorders using an extract from the leaves and roots of the plant Mullein.

Historically, the plant Mullein, genus Verbascum, has been used in a variety of different ways in the practice of herbal medicine. For example, the leaves of mullein have been smoked as a treatment of asthma. Leaf infusions have been taken for the treatment of coughs, catarrh, tuberculosis, hemoptysis, long standing diarrhea, dysentery, gout, rheumatism, and hemorrhoids. In the treatment of coughs and bowel disorders, the leaves have been boiled in milk for 10 minutes and seasoned or sweetened if desired. J. F. Morton, *Folk Remedies of the Low Country*, 155–156.

A leaf infusion has been applied externally to hemorrhoids, ulcers and tumors. An ointment for the treatment of wounds can be made by boiling mullein leaves with lard. A poultice including mullein with flax seed meal can be placed on burns, scalds and boils. Additionally, a poultice including an infusion of the leaves and pith of the stem in hot vinegar or water has been laid on the throat to treat cynanche tonsillaris, cynanche maligna and mumps. A poultice of fat and mullein leaves has been used to draw boils to a head. J. F. Morton, *Folk Remedies of the Low Country*, 155–156.

It will be appreciated by those skilled in the art that certain skin disorders are difficult to treat effectively. For example, actinic keratosis, a pre-malignant skin condition related to aging and to sun exposure, is generally treated with cryotherapy. In this process, an extremely cold liquid is applied to the keratosis, effectively freezing and killing the affected tissue. This process often leaves scars on the patient where the treatment occurs. Additionally, the actinic keratoses often return, thus requiring more cryotherapy and more potential scarring. If left untreated, actinic keratosis can become a form of skin cancer, squamous cell carcinoma.

Inflammatory conditions of the skin are often difficult to treat effectively as well. An example of an inflammatory skin condition that is difficult to treat is psoriasis. Treatments for psoriasis are often complex and uncomfortable to the patient. One treatment involves the application of a prescribed medication, such as a corticosteroid, to the skin and the subsequent covering of the skin with an occlusive dressing. As psoriasis is a chronic condition, the complicated treatment procedure must be repeated as the condition recurs.

Malignant melanoma is a form of skin cancer that is also difficult to treat. Early diagnosis is a key to patient survival of this disease. The lesions of malignant melanoma are typically removed surgically from the skin.

What is needed, then, is an effective treatment for these and similar disorders. Additionally, a treatment that does not involve difficult or damaging treatment procedures is also needed. Such methods of treatment is presently lacking in the prior art.

SUMMARY OF THE INVENTION

It is an object of this invention to provide an effective treatment for skin disorders including sun exposure related and aging related skin disorders like actinic keratoses, lentigines (age spots), seborrheic keratoses, and the inflammatory skin disorders such as prurigo, psoriasis, and contact dermatitis.

It is a further object of this invention to provide a treatment for the skin cancer, malignant melanoma.

It is a further object of this invention to provide a method of treatment for the above described skin disorders and similar disorders which does not involve difficult or damaging treatment procedures.

The method of treating the above mentioned disorders comprises applying a liquid extract from the plant Mullein (genus Verbascum) to affected areas of the patient's skin. In the preferred embodiment of this invention, this extract is formed by cooking the leaves and roots of the plant Mullein in a pressure cooker with water. The resulting extract is then canned according to standard home canning procedures.

DESCRIPTION OF THE PREFERRED EMBODIMENT

The composition that is used in the method of this invention is derived from the plant Mullein, genus Verbascum. One particular species of the plant that is used is the species, *V. thapsus*. Leaves and roots, preferably from the first year stage of the plant Mullein in which the plant has no flowers or seeds, are collected and cut into pieces. Preferably, the pieces are then cooked in a pressure cooker in water. The resulting liquid extract is canned using common home canning procedures. The extract must be refrigerated after opening. To prepare approximately one gallon of extract, approximately one-half pound of first stage leaves and roots are used. Generally, it takes about four plants to accumulate one-half pound of leaves and roots, with the leaves of these plants being approximately one foot in length.

The extract, which has a watery consistency, is applied to an affected area as follows. The liquid is wiped on the affected area and the skin is allowed to dry. Typically, the extract is applied twice a day, once in the morning and once in the evening. The extract is applied as long as needed, but, as more fully described below, subjects usually experience improvement in their conditions after a period of approximately two weeks. The subjects experience a slight tingling and a slight tightening sensation after the extract is applied.

It is contemplated that composition used in the method of treating skin disorders described in this invention also includes any composition containing a synthetically produced component or components of the extract from the plant Mullein.

The following non-limiting examples illustrate the utility of the method and composition of this invention in treating various skin disorders.

EXAMPLE 1

Subject No. 1, a middle aged white male, was diagnosed as having actinic keratoses, a premalignant skin disorder related to sun exposure and related to aging. Actinic keratoses are raised scaly spots in the epidermis of the skin. Subject No. 1 received treatment for the actinic keratoses in the form of cryotherapy. The cryotherapy froze and destroyed the actinic keratoses, but the treatments left the subject with many scars on his arms.

The actinic keratoses returned after these treatments. Rather than continue the cryotherapy, Subject No. 1 applied the extract of the present invention to the affected areas on his arms. The extract was wiped onto the skin as a liquid twice a day. The skin was then allowed to dry. This procedure was continued for a period of 12 days. After three days, the actinic keratoses became dark, but the subject kept applying the extract. After 12 days, the actinic keratoses had cleared up completely. No scarring, as described above with the cryotherapy, occurred using the extract as a treatment. Subject No. 1 visited his doctor to confirm that the spots were gone. The doctor confirmed this and did not recommend any further cryotherapy.

EXAMPLE 2

Subject No. 2, a middle-aged white female, was diagnosed as having psoriasis. Particularly, she was diagnosed as having chicken skin psoriasis. Subject No. 2 was required to put a prescribed ointment on her arms and sleep in long gloves as a part of her treatment. These treatments were administered on an ongoing basis, as Subject No. 2's psoriasis recurred as a chronic condition.

Subject No. 2 applied the extract of the present invention to the affected areas on her arms. As described above, the extract was wiped onto the skin as a liquid twice a day, and the skin was then allowed to dry. This procedure was continued for approximately 2 weeks. After using the extract of the method in the present invention for 3 weeks, Subject No. 2's psoriasis has effectively cleared. This conclusion was confirmed by her doctor.

EXAMPLE 3

Subject No. 3, a teenaged white male, and the son of Subject No. 2, was also diagnosed as having chicken skin psoriasis. He also applied the extract used in the method of this invention twice a day for a period of approximately 3 weeks. After using the treatment of this invention, Subject No. 3's psoriasis has also disappeared. This conclusion was also confirmed by his doctor.

EXAMPLE 4

Subject No. 4, a 55 year old white male, was diagnosed as having malignant melanoma and its pre-malignant precursors on his face and nose. Doctors removed the lesions of this condition in previous treatments. However, the lesions recurred.

Subject No. 4 followed the method of treatment for this invention for a period of 4 weeks. The melanoma cleared after this period of treatment.

EXAMPLE 5

Subject No. 5, a white male, 73 years of age, was diagnosed as having the skin cancer malignant melanoma. Many of the cancerous lesions were surgically removed. Other pre-cancerous spots continued to appear on his skin after the surgical procedures.

Subject No. 5 applied the extract of this invention twice a day to these pre-cancerous spots for a period of 4 weeks. These spots cleared before they turned to cancer.

EXAMPLE 6

Subject No. 6, a white male, was diagnosed as having the skin cancer malignant melanoma on his head. After following the treatment described in the present invention for two weeks, the his head was clear of this skin cancer.

EXAMPLE 7

Subject No. 7, a white female, was diagnosed as having psoriasis on her head. Smaller spots of psoriasis have disappeared since using the treatment described in the present invention twice a day. A larger lesion was reduced in size by 75% after following the treatment of this invention for seven days.

EXAMPLE 8

Subject No. 8, a middle-aged white male, was diagnosed as having the severe skin condition, Prurigo, on his arms and head. Prurigo, an inflammatory skin condition, is characterized by the appearance of weeping sores on the arms and head of the sufferer. Currently, there is no known cure of Prurigo. After applying the treatment of this invention twice a day for a period of two weeks, Subject No. 8's arms were clear of the weeping sores and his head is approximately 75% clear of the sores. The remaining 25% of the sores exhibited considerable improvement.

EXAMPLE 9

Subject No. 9, a white female, noticed the appearance of dark pigment spots on her skin. These spots were characterized as sun spots or age spots. These sun spots are also referred to as lentigines. She applied the treatment of this invention twice a day for a period of 3 weeks. The dark spots disappeared after using the treatment of this invention.

EXAMPLE 10

Subject No. 10, a white male, noticed the appearance of dark pigment spots on his skin. These dark pigment spots were diagnosed as seborrheic keratoses. Subject No. 10 also suffered from acne. After applying the treatment of this invention twice a day for a period of approximately 2 weeks, Subject No. 10 observed the disappearance of the seborrheic keratoses. Subject No. 10 has also noticed that great improvement in the acne condition.

EXAMPLE 11

Subject No. 11, a white female, suffered from a rash caused by a metal bracelet that she was required to wear that indicated that she was a diabetic. This rash was unsuccessfully treated by a dermatologist. Subject No. 11 applied the liquid extract of the method of this invention twice a day. After a period of 12 days, the rash disappeared.

EXAMPLE 12

Subject No. 12, a white female, suffered from a chronic rash on her neck for years. Her condition was not improved by an application of a prescription treatment. After applying the treatment of this invention twice a day for a period of two weeks, her rash was gone.

Although there have been described particular embodiments of the present invention of a new and useful Method of Treating Skin Disorders Using an Extract of Mullein, it is not intended that such references be construed as limitations upon the scope of this invention except as set forth in the following claims. Further, although there have been described certain examples used in the preferred embodiment, it is not intended that the described ratios be construed as limitations upon the scope of this invention except as set forth in the following claims.

What is claimed is:

1. A method of treating a skin condition of a patient in need thereof, comprising applying a therapeutically effective amount of a composition including an extract of a mullein plant to an affected area of said skin, wherein said skin condition is selected from the group consisting of: actinic keratosis, lentigines, seborrheic keratosis, psoriasis, and contact dermatitis.

2. The method of claim 1, wherein said skin condition is actinic keratosis.

3. The method of claim 1, wherein said skin condition is lentigines.

4. The method of claim 1, wherein said skin condition is seborrheic keratosis.

5. The method of claim 1, wherein said skin condition is psoriasis.

6. The method of claim 1, wherein said skin condition is contact dermatitis.

7. The method of claim 1, further comprising creating said extract of a mullein plant by boiling leaves and roots of said mullein plant in a solvent.

8. The method of claim 7, wherein said solvent is water.

9. The method of claim 1, further comprising creating said extract of a mullein plant by boiling leaves and roots of said mullein plant in water in a pressure cooker.

10. The method of claim 1, wherein said applying step includes applying said composition daily.

11. The method of claim 1, wherein said mullein plant is a *Verbascum thapsus* plant.

12. A method of treating a skin condition of a patient in need thereof, comprising applying a therapeutically effective amount of a composition including an extract of a *Verbascum thapsus* plant to an affected area of said skin, wherein said skin condition is selected from the group consisting of: actinic keratosis, lentigines, seborrheic keratosis, psoriasis, and contact dermatitis.

13. The method of claim 15, wherein said skin condition is actinic keratosis.

14. The method of claim 15, wherein said skin condition is lentigines.

15. The method of claim 15, wherein said skin condition is seborrheic keratosis.

16. The method of claim 15, wherein said skin condition is psoriasis.

17. The method of claim 15, wherein said skin condition is contact dermatitis.

18. The method of claim 15, further comprising creating said extract of a mullein plant by boiling leaves and roots of said *Verbascum thapsus* plant in a solvent.

19. The method of claim 18, wherein said solvent is water.

20. The method of claim 15, further comprising creating said extract of a mullein plant by boiling leaves and roots of said *Verbascum thapsus* plant in water in a pressure cooker.

21. The method of claim 15, wherein said applying step includes applying said composition daily.

\* \* \* \* \*